United States Patent [19]
Chavanne et al.

[11] Patent Number: 6,144,456
[45] Date of Patent: Nov. 7, 2000

[54] APPARATUS HAVING A MULTIPLE ANGLE TRANSPARENT ROTATING ELEMENT FOR MEASURING THE THICKNESS OF TRANSPARENT OBJECTS

[75] Inventors: Philippe Chavanne, Aclens; Rene Paul Salathe, Ecublens, both of Switzerland

[73] Assignee: Haag-Streit AG, Bern-Koniz, Switzerland

[21] Appl. No.: 08/945,792

[22] PCT Filed: May 6, 1996

[86] PCT No.: PCT/CH96/00172

§ 371 Date: Nov. 4, 1997

§ 102(e) Date: Nov. 4, 1997

[87] PCT Pub. No.: WO96/35100

PCT Pub. Date: Nov. 7, 1996

[30] Foreign Application Priority Data

May 4, 1995 [CH] Switzerland .............................. 1294/95

[51] Int. Cl.$^7$ ...................................................... G01B 9/02
[52] U.S. Cl. ........................... 356/479; 356/497; 356/503
[58] Field of Search ................................... 356/355, 357, 356/345, 346, 358; 250/227.19, 227.27; 385/12; 351/211, 212, 221; 600/318

[56] References Cited

U.S. PATENT DOCUMENTS

| | | | |
|---|---|---|---|
| 3,482,919 | 12/1969 | Barringer | 356/346 |
| 3,776,637 | 12/1973 | Hecht | 356/345 |
| 5,491,524 | 2/1996 | Hellmuth et al. | 351/221 |
| 5,537,162 | 7/1996 | Hellmuth et al. | 351/221 |

FOREIGN PATENT DOCUMENTS

| | | | |
|---|---|---|---|
| 3446014 | 6/1986 | Germany | 356/345 |

OTHER PUBLICATIONS

"Absolute optical ranging using low coherence interferometry", Danielson et al, Applied Optics, Jul. 1991, pp 2975–2979.

"Pathlength alteration in an interferometer by rotation of a retroreflector", Tank, Mikrochimica Acta, 1998, pp319–321.

*Primary Examiner*—Samuel A. Turner

[57] ABSTRACT

The apparatus for measuring the thickness of transparent objects (1) has a radiation source (3) of short coherence length and a Michelson interferometer (5), wherein the object (1) to be measured can be arranged in its measuring arm (11), and path length variation element (15), which has an optical path length that changes periodically due to its own rotation, is arranged in the reference arm (13). The cross-sectional surface (34) of the element (15) wherein the reference beam comes to rest has at least four corners so that the reference radiation path in the element (15) has at least two reflections on the inner surfaces of the element. The reference beam (41e) coming out of the element (15) is reflected back by means of a fixed reflector (30) into the element (15), preferably into itself.

The measurements of the side surfaces of the element (15), the beam entry location therein, as well as the index of refraction of the element material can be selected in such a way that the path length difference obtained by means of the rotating element (15) runs approximately linearly to the rotation angle in a preferred embodiment. This linearity results in a reduced bandwidth of the Doppler frequency of the radiation irradiating on the object (1). This reduced bandwidth of the Doppler frequency allows an excellent filtration and results thereby in a reduced signal-noise ratio of the measuring signal.

9 Claims, 3 Drawing Sheets

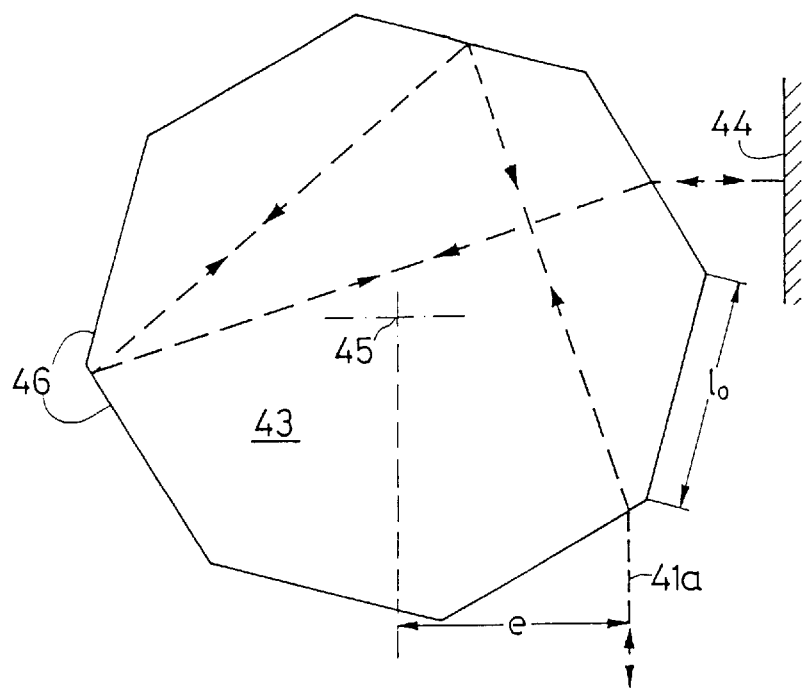
Fig. 7
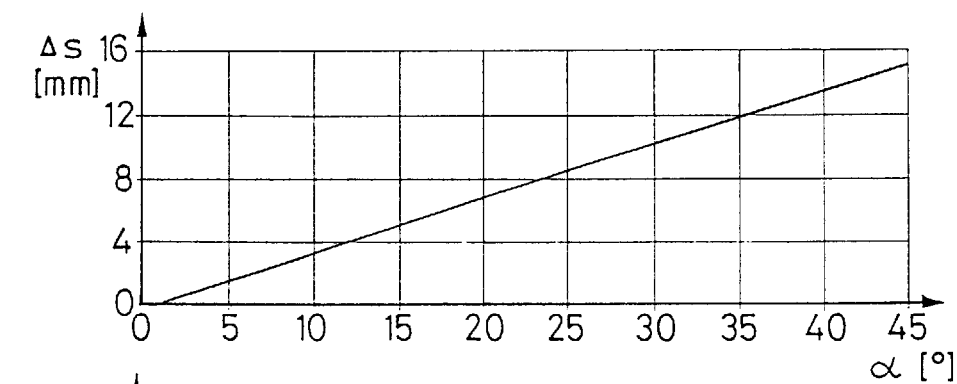
Fig. 8
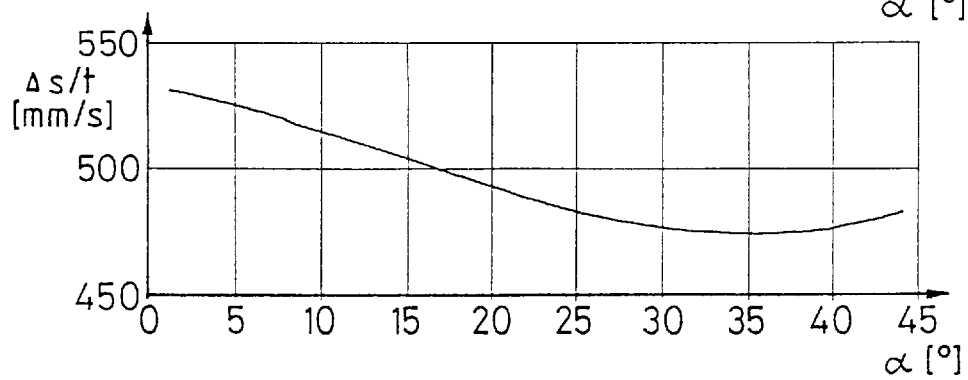

APPARATUS HAVING A MULTIPLE ANGLE TRANSPARENT ROTATING ELEMENT FOR MEASURING THE THICKNESS OF TRANSPARENT OBJECTS

BACKGROUND OF THE INVENTION

1. Field of the Invention

The invention concerns an apparatus for measuring the thickness of transparent objects.

2. Description of the Background Art

It is known in the art to use an interferometer for measuring the thickness of transparent objects, particularly a Michelson interferometer. This interferometer has a beam splitter, a so-called coupler that splits a beam generated by a radiation source into two partial beams: a measuring beam and a reference beam. These are guided toward each other after a certain distance, are superposed in the beam splitter, and are then sent back partially into the radiation source or irradiated into an observation detector. If a radiation source that has a radiation with a short coherence length is used, the interference between reference and measuring beam is maintained only when both of their paths are exactly equal in length. This interference can be determined by means of the observation detector.

The beam splitter only initially changes the length of the reference path with a modification speed that is as constant as possible, until the interference of the radiation leaves the reference and measuring paths for determining the distance values of an object with a surface that must reflect merely a reduced fraction of the radiation. Depending upon the modification speed, the radiation frequency f of the radiation source that runs in the reference path undergoes a Doppler displacement according to the relationship $$\frac{\Delta f}{f_0} = \frac{2v}{c}$$

wherein $f_0$ represents the original radiation frequency, c represents the light speed, and v represents the speed of modification of the optical path length ▲s—the optical path length modification per time unit.

If an interference occurrence with equal reference and measuring paths can be detected with the observation detector, then the interference pattern is modified according to the above Doppler displacement with the frequency ▲f. ▲f is a time constant if there is a strictly linear modification of the path length difference. If non-linear path length modifications appear, then ▲f varies within the frequency band.

Michelson interferometers wherein the path length modifications are generated in the reference path are known, for example, from EP-A 0,529,603, EP-A 0,443,477, and EP-A 0,449,335. A retroreflector is arranged in each arm of the interferometer in EP-A 0,529,603. Each retroreflector was displaceable by means of a gear that had a toothed belt, so that each front side of the reflector on the surface of a fixed reflector remained parallel even with a distance modification to a fixed reflector. The distance modification took place in such a manner that the optical path length increased in the interference arm, while it decreased in the other. Since both of the drives had to be synchronized, the drive was carried out by means of an electric stepper motor. This arrangement was complicated and also disturbing mechanical oscillations were caused by means of the electric impulse of the stepper motors.

Two retroreflectors per interference arm, which rotated in opposite directions to one another were used in EP-A 0,443,477, plus a further retroreflector that deviated the radiation, as well as a fixed plane level. A synchronization between the rotation of the reflectors was required here also, which was carried out as well by means of the mechanical oscillations of stepper motors.

A thick transparent plane-parallel plate was used in EP-A 0,449,335 for modifying the path length difference in both interference arms. The plate was traveled by the radiation in one direction as well as in the return direction after reflection on the fixed reflector, and the optical path changed according to the inclination of the plate.

The known elements for modifying the path length difference between measuring and reference beam show either a complicated mechanical arrangement that is therefore a vibration-susceptible arrangement and/or a considerable non-linear path difference modification.

SUMMARY OF THE INVENTION

The object of the invention is to provide an apparatus that allows accurate measurement of the thickness of transparent objects by means of a simple arrangement that is resistant to disturbances.

Contrary to the known apparatus, the object of the invention is attained in that not more than one or more retroreflectors or one plane-parallel plate that has been irradiated only once are being used, but a multiple angle transparent rotating element is used that has at least four corners. The measurements of the side surfaces of the element and the location where the same is irradiated, as well as the index of refraction of the material of the element are selected in such a way that the path length difference obtained with the rotating element that changes over time runs approximately in a linear fashion over the rotation angle.

The apparatus of the invention is particularly suitable for determining the thickness of transparent mediums with surfaces that are unreachable or are difficult to reach. It allows thickness measurements wherein the delimiting surfaces have only a low reflectivity. The great sensing speed of the apparatus of the invention should be noted, which also allows to carry out measurements as well as observations on objects in motion, particularly in rapid processes wherein materials are removed or applied onto the object to be measured.

Finally, it is noted that the rotating elements that cause a path length modification can be installed in the measuring unit as well as in the reference unit, since it depends merely upon the path length difference in both arms (measuring arm/reference arm). Two elements that rotate in opposite directions can also be used by installing one in each arm. This way, an expansion of the variation range and the sensing speed can be obtained. The exact angle positioning of the element, which indicates the additive path length, can be determined, for example, by means of known coding discs.

A considerable modification possibility of the path difference is obtained by bending the beam within the element via multiple reflections.

Also, in contrast to the known apparatus, only a single simply-driven element is used which rotates around one axis. A vibration-free, direct-current motor can be used as a drive. A synchronous running of several elements that must be supervised and controlled is thereby omitted and, therefore, the production of mechanical vibrations is avoided, which occurs with the commonly used stepper motors of the known apparatus.

A problem-free coupling of the object to be measured is obtained by using a radiation guide, particularly in the measuring arm. A simple and room-saving path adaptation is possible if the reference arm is also provided with a radiation guide. An interference between the reference radiation and the measuring radiation reflected on the surface of the object to be measured is obtained when determining the thickness of transparent objects. The transfer from one medium into another medium with a different refraction index generates the reflected measuring radiation.

An excellent linearity of the path length modification, which in turn produces a reduced bandwidth of the Doppler frequency, can be obtained by means of the geometry described below as well as the optimized selection of the measurements and the irradiation location, and also by means of the index of refraction of the rotating element. This reduced bandwidth of the Doppler frequency allows an excellent filtration resulting in a large signal-noise ratio. Due to the large signal-noise ratio obtained, it is possible to measure thicknesses of transparent objects wherein a change in the index of refraction between the material of the object to be measured and the environment is very small. The below-described measuring arrangement is sensitive to the extent that thicknesses of objects can be determined which, for example, have a radiation reflection of 4% on the front surface and a degree of reflection of merely $10^{-8}$ in the rear surface. The degree of reflection of the front surface can also be high, such as, for example, in a metallic mirror; a measurement through this metallic mirror is made possible in this manner. The apparatus of the invention can also be utilized with a small front surface reflection and a large rear surface reflection. The invention is suitable particularly for measuring the cornea of the human eye, which has a front surface reflection of 2.5% and a rear surface reflection of $2.2-10^{-4}$.

BRIEF DESCRIPTION OF THE DRAWINGS

Examples of the apparatus of the invention are further described through the following drawings. Further advantages of the invention become apparent from the following description, wherein:

FIG. 7 is a representation similar to the one shown in FIGS. 3 to 4 of the path length variation element in the shape of an octagon; and, FIG. 8 is a representation similar to the one shown in FIG. 5 of the path length variation element shown in FIG. 7.

DETAILED DESCRIPTION OF THE PREFERRED EMBODIMENTS

Figure 1:
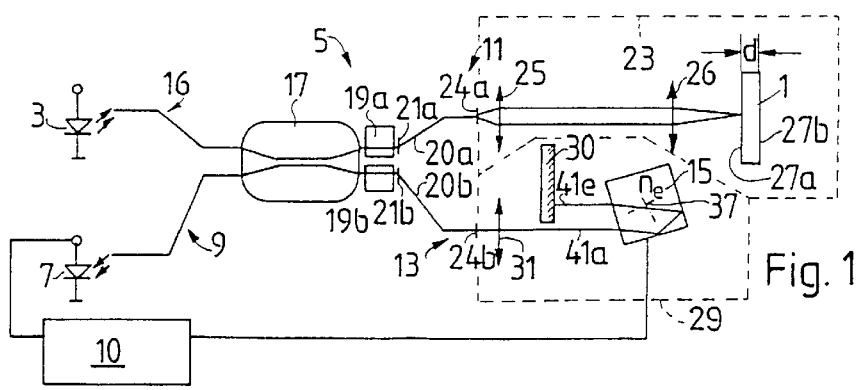
FIG. 1 is a block circuit diagram of an apparatus for measuring the thickness of transparent objects.

The apparatus for measuring the thickness d of a transparent object 1 shown in the block circuit diagram of FIG. 1 has a super luminescence diode as its radiation source 3, which has a short coherence length in the range of approximately 10 to 15 μm, a Michelson interferometer 5, and a radiation detector 7 in the observation arm 9, which operates together with an evaluation unit 10. The object 1 is arranged in the measuring arm 11 of the interferometer 5 and the path length variation element 15, which can be rotatably displaced, is arranged in the reference arm 13.

The measuring, reference, illumination, and observation arms 11, 12, 16, or 9 are connected to each other by means of a 50/50% coupling 17. A polarization control unit 19a or 19b is arranged in the measuring and reference arms 11 and 13 ahead of the connection to the coupling 17. A radiation guide 20a with a removable coupling 21a, which leads to a measuring unit 23, is connected to the polarization control unit 19a in the measuring arm 11. The measuring unit 23 is also connected to the other end of the radiation guide 20a also by means of a removable coupling 24a. The measuring unit 23 has a lens 25 for collimating the radiation guided by means of the radiation guide 20a, as well as a focusing lens 26 for focusing the emitted radiation and for gathering the radiation reflected from the object surfaces 27a and 27b. The focusing lens 26 is preferably arranged in such a way, that the radiation is bundled from the rear surface 27a, which has a very small degree of reflection—see the preferred embodiment.

A radiation guide 20b with a removable coupling 21b, which leads to the reference unit 29 with the path length variation element 15 and a reflector 30 connected behind it, is also connected to the polarization control unit 19b of the reference arm 13. The other end of the radiation guide 20b is also connected to the reference unit 29 by means of a removable coupling 24b. The radiation guided by means of the radiation guide 20b is collimated by means of the lens 31 in the reference unit 29 and irradiated into the element 15.

The radiation guide in the reference and measuring arms 13 and 11 is preferably selected in such a way that the differences in the dispersion within both arms 11 and 13 are negligible, so that no dispersion of the interference signal occurs.

Figure 2:
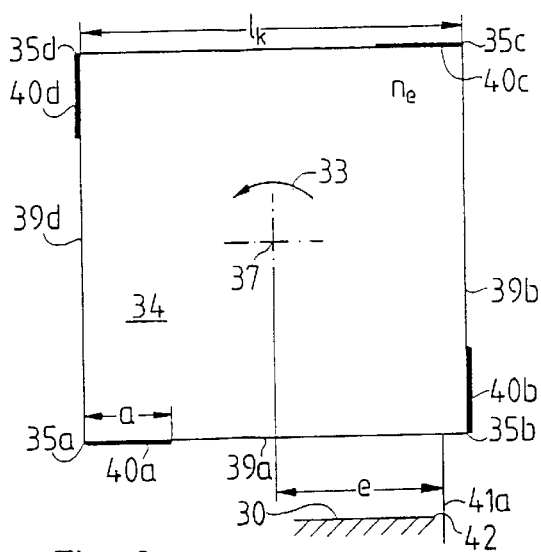
FIG. 2 is an enlarged representation of the path length variation element with reflector in the reference arm of the apparatus represented in FIG. 1, wherein precisely one side of the path length variation element is parallel to the reflector surface.
Figure 3:
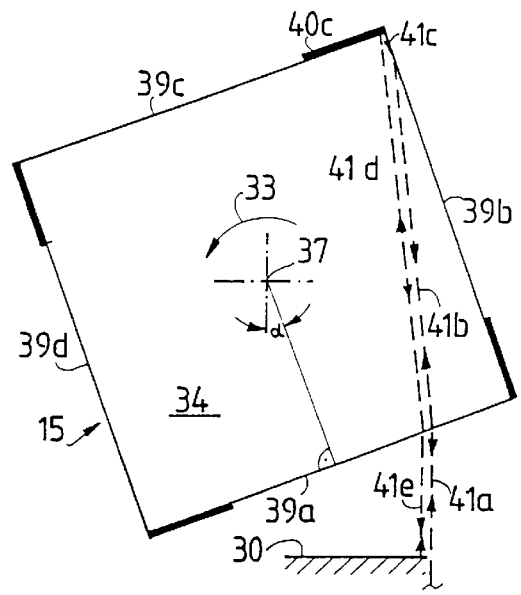
FIG. 3 is a representation of the element with beam passage similar to the one shown in FIG. 2, but displaced with respect to the representation of FIG. 2 by 20, and in FIG. 4 the same is rotated by 40°, wherein the coatings 40a to 40d of FIGS. 2 to 4 stand out.
Figure 4:
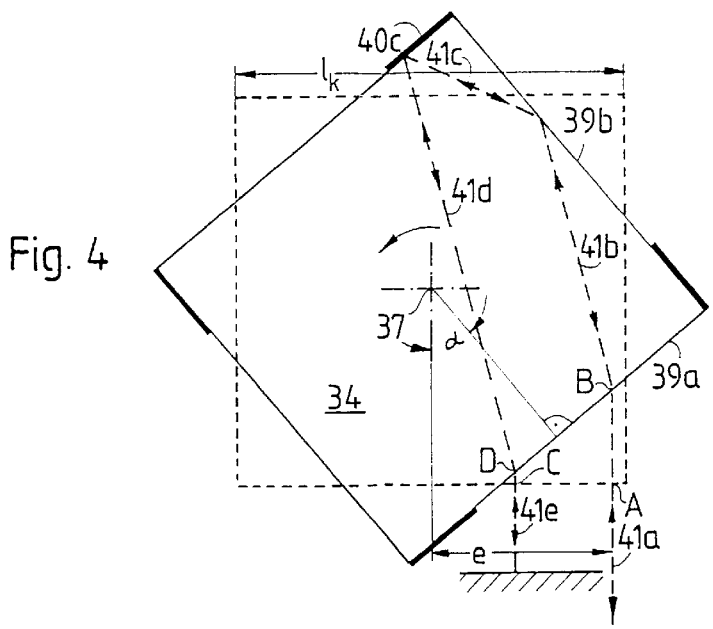

FIGS. 2 to 4 show arrangements of the path length variation element 15 with a reflector 30 in an enlarged representation with respect to FIG. 1. The element 15 is displaceable into rotation according to arrow 33 by means of a drive, which is not represented. The cross-section surface 34 of the element 15, wherein the reference beams 41b, 41c, and 41d come to rest, has four corners 35a to 35d and a quadratic shape in the embodiment selected here; that is, the element is a straight cylinder with a quadratic surface area. The rotation axis 37 is identical to the axis of the cylinder. Each cylinder jacket surface 39a to 39d of the element 15a is provided with a partial coating 40a to 40d, which is selected so that the beams 41c or the retroreflected beams 41d of the radiation which are present within the element 15 are optimally reflected. No reflection coating is necessary on the reflection location of the beam 41b or the beam 41c that is retroreflected onto the wall 39b shown here as an example, since there is a complete reflection. The coatings 40a to 40d start at each of the corners (edges) 35a to 35d and extend over a distance into the corresponding side surfaces 39a to 39d. Starting from each edge 35a to 35d, only one of the two impacted sides is coated and precisely only always those where the reflected beam together with the entering beam form an acute angle, see particularly FIG. 3 with respect to this.

The instant position of the rotating element 15 illustrated in FIG. 2 shows its side 39a standing in a parallel position to the surface of the reflector 30. The reference beam 41a, which enters into the element 15, is guided in such a way that it can be lead precisely by the right edge 42 of the reflector 30 shown in FIGS. 2, 3, and 4. The distance e from the reflector edge 42 is precisely so dimensioned that it is only slightly smaller than the half cube edge. In the numerical example selected herein, which has a surface width $1_k$ of 30 mm, the reference beam 41a is irradiated at a distance e of 13 mm from the center rotation axis 37 and a distance of approximately 3 mm from the reflector edge 42.

FIG. 3 shows the element 15 rotated with respect to the representation of FIG. 2 by an exemplary angle $\alpha$ of 20. The beam 41a penetrates under refraction as beam 41b into the transparent medium of the object 15 and is completely reflected on the surface 39b. The entering and reflected beams 41b and 41c together form an obtuse angle. The reflected beam 41c enters at the lower side of the surface 39c and is reflected there by the coated area 40c as beam 41d in the direction of the surface 39a parallel to the beam 41b. Both beams 41c and 41d together form an acute angle. The beam 41d entering the surface 39a is refracted and enters as beam 41e vertically into the reflector 30 and is there reflected back again onto itself in complete reflection, so that the beam reflected onto the reflector 30 leaves at the location of the entrance of the beam 41a with the same direction of the beam 41a. As can be seen in a comparison with FIGS. 3 and 4, the reflection point of the beam 41e on the reflector 30 wanders back and forth.

Due to the rotation of the element 15, the path length modification AS is comprised by the double path of the changing path lengths of the beams 41a to 41e. It must be noted, for the beams 41b to 41d, that their path lengths are increased by the refraction index n of the medium wherein they run. According to FIG. 4, a path length s dependent upon the rotation angle $\alpha$, the distance of the beam entrance e, the refraction index $n_e$, and the surface width $1_k$ of the surfaces 39a to 39d. The path length s calculated below begins and ends at the striped straight lines A–D of FIG. 4, which reproduce the position of the element 15 shown in FIG. 2.

$$s = n_e(41b+41c+41d)+CD+AB$$

$$41b+41c=41d, \text{ consequently}$$

$$s = 2 \cdot n_e \cdot 41d + CD + AB,$$

wherein the distance $41d = 1_k \cdot [1-(\sin \alpha)^2/n_e^2]^{-1/2}$ the distance CD $$CD = \frac{Z_{CD,1} \cdot Z_{CD,2}}{N_{CD}}$$

with $$N_{CD} = n_e \cdot [1-\sin \alpha^2/n_e^2]^{1/2} + \frac{1}{2}[1_k - 1_k \cdot \tan(\alpha/2)] \cdot \tan \alpha,$$

$$Z_{CD,1} = -2 \cdot \sin \alpha^2 \cdot (1_k - n_e \cdot \sin \alpha^{-1} \cdot (1-\sin \alpha^2/n_e^2)^{1/2},$$

$$Z_{CD,2} = [1_k/2 + 1_k \cdot \tan(\alpha/2)/2 - \cos \alpha^{-1} \cdot [1_k/2 - 1_k \cdot \tan(\alpha/2)/2]$$

and the distance $AB = \frac{1}{2} \cdot [1_k - 1_k \cdot \tan(\alpha/2)] \cdot \tan \alpha$.

Figure 5:
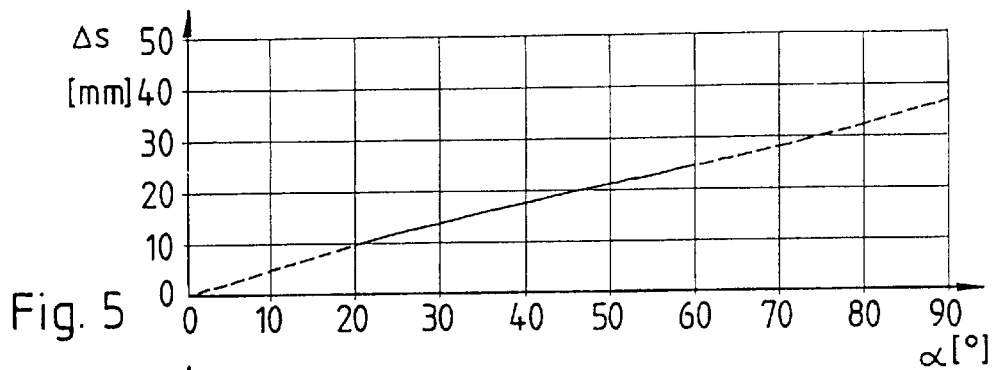
FIG. 5 shows, in the top illustration, the path length difference ▲s (mm) over the rotation angle α of the element with a side length $1_k$ of 30 mm, a distance e of 13 mm, and an index of refraction $n_e$ of the material of the element of 1.5, wherein the striped curve values provide values which cannot be obtained with the elements shown in FIGS. 2 to 4, since the element surfaces have a partial reflection coating starting from each of the element edges; the bottom curve shows the path length modification αs/t in dependence upon the rotation angle corresponding thereto.
Figure 5:
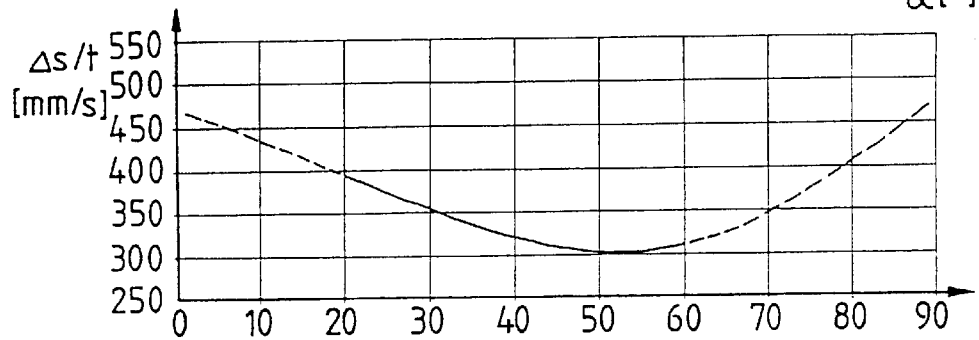
Figure 6:
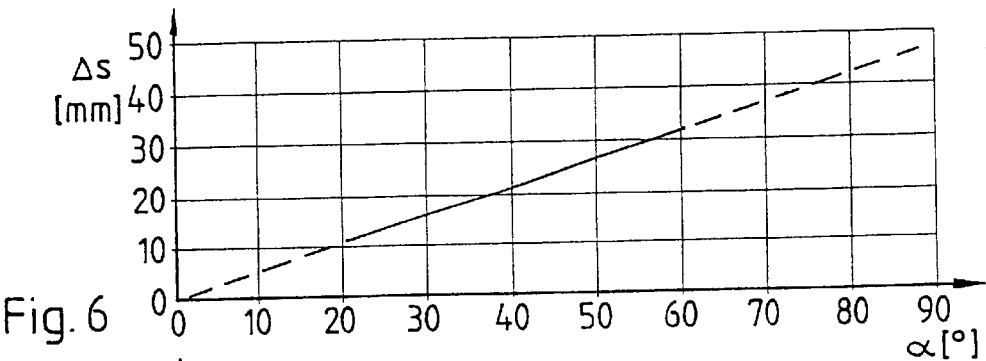
FIG. 6 is a representation similar to the one shown in FIG. 5, but with an index of reflection of $n_e=2.5$.
Figure 6:
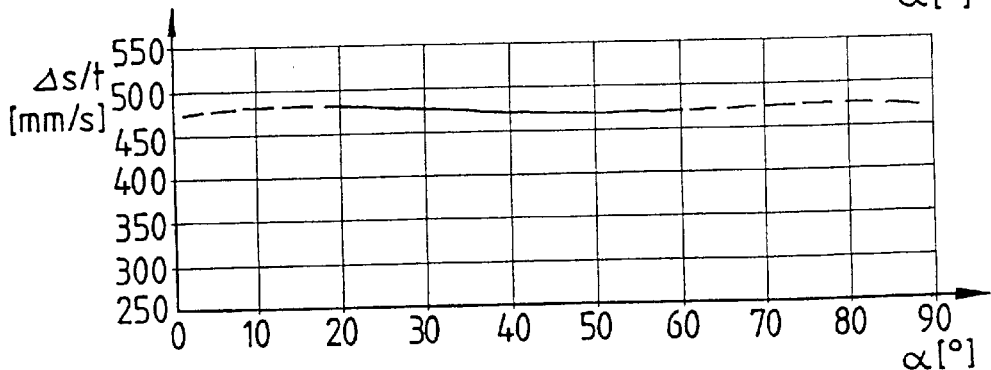

The parameters e, $1_k$, and $n_e$ can only be optimized in that, for the preset angle range $\alpha$, an approximately linear path length modification v can be obtained as path differential as shown in FIGS. 5 and 6. The path length variation as time derivate of the path length variation results in $$v = \frac{ds}{dt} \frac{ds}{d\alpha},$$

wherein w represents the angle speed of the rotating element 15. The determined time path length modification v and the difference frequency ▲f, that can be measured with the radiation detector, are connected by means of the relationship $$\blacktriangle f = \frac{2 \cdot f_0 \cdot v}{c}$$

The path length variations v result in $$v = \frac{Z_{v,1} - Z_{v,2} \cdot Z_{v,3}}{N_{v,1}} - \frac{Z_{v,4} \cdot Z_{v,5}}{N_{v,2}} - Z_1 -$$
$$2 \cdot \sin \alpha^2 / N_{v,2} \cdot [Z_{v,3} \cdot \cos \alpha + Z_{v,6} \cdot Z_{v,7} \cdot (Z_{v,8} - Z_{v6})]$$

with $$Z_{v,1} = \frac{2 \cdot 1_k \cdot \cos \alpha \cdot \sin \alpha}{n_e [1 - \sin \alpha^2 / n_e^2]^{3/2}} + 2 \cdot \cos \alpha^{-2} \cdot \frac{1}{2} \cdot 1_k [1 - \tan(\alpha/2)];$$

$$Z_{v,2} = 2 \cdot \cos \alpha \cdot \sin \alpha^3 \cdot [1_k - n_e \cdot \sin \alpha^{-1} \cdot [1-\sin \alpha^2/n_e^2]^{1/2};$$

$$Z_{v,3} = 1_k/2 \cdot [1+\tan(\alpha/2) - \cos \alpha^{-1} \cdot (1-\tan(\alpha/2)];$$

$$N_{v,1} = n_e \cdot (1-\sin \alpha^2/n_e^2)^{3/2};$$

$$Z_{v,4} = 4 \cdot \cos \alpha \cdot \sin \alpha \cdot (1_k - n_e \cdot \sin \alpha^{-1} \cdot (1-\sin \alpha^2/n_e^2)^{1/2};$$

$$Z_{v,5} = 1_k/2 \cdot [1+\tan(\alpha/2) - \cos \alpha^{-1} \cdot (1-\tan(\alpha/2)];$$

$$N_{v,2} = n_e \cdot (1-\sin \alpha^2/n_e^2);$$

$$Z_1 = \frac{1}{2} \cdot [1_k \cdot \sin(\alpha/2)^{-2} \cdot \tan \alpha];$$

$$Z_{v,6} = n_e \cdot \cot g \alpha \cdot \cos \alpha^{-1} \cdot [1-\sin^2 n_e^2];$$

$$Z_{v,7} = Z_{v,3} - n_e \cdot \cos \alpha^{-1} \cdot [1-\sin \alpha^2/n_e^2]^{1/2};$$

$$Z_{v,8} = 1_k/4 \cdot [\sin(\alpha/2)^{-2} + (\sin(\alpha/2)^{-2} \cdot \sin \alpha^{-1});$$

$$Z_{v,9} = 1_k/2 \cdot \sin \alpha^{-1} \cdot \tan \alpha \cdot [1-\tan(\alpha/2)].$$

To achieve a compact construction, the distance of the reflector 30 from the rotation axis 37 to the element 15 is just large enough to provide a disturbance-free rotation of the edges 35a–d.

A larger rotation angle ▲$\alpha$ of the element 15 with respect to the representation shown in FIGS. 5 and 6 can be used if the coating 40a to 40d is omitted. The intensity available for interference is, however, more reduced but still sufficient, since a good filtration possibility is provided due to the good linearity of the path difference modification ▲s/t.

The multiple reflections, which lie in the vicinity of the beam paths shown in FIGS. 3 and 4, do not cause disturbances, since they do not reach into the beam guide 20b due to the good screening effect of the coupling into the same.

The radiation signal received by the radiation detector 7 is transformed into an electric signal for signal evaluation. The electric frequency, which corresponds to the Doppler frequency displacement ▲f of the radiation, is filtered by means of the experimental construction and is only processed to obtain the highest possible signal-noise ratio. The minimum b an d width is determined by means of the inverted measuring time for the half coherence length of the radiation wave. The signal evaluation is carried out in dependence upon the angular position of the rotation angle α, which corresponds to a certain position of the element 15 and which, therefore, corresponds to a preset path difference ▲s, taken from an angle transmitter of the element 15.

In case the remaining non-linearity in the expression ds/dα leads to large bandwidths, the work can be carried out with either larger filter bandwidths, which bring with them a reduced signal-noise ratio, or the utilized angle area is reduced until the minimum bandwidth is reached again. The last named possibility effects a reduction of the measuring area which, however, is compensated by an increase of the cube edge length $1_k$.

If the object 1, which is transparent to the radiation of the radiation source 3, is located in the measuring arm 11, then an electric signal of the Doppler frequency displacement with the frequency ▲f is obtained each time, that ▲s, if the paths in the measuring and reference arms 11 and 13 have the same length. The path length difference ▲s generated with the element 15 must therefore be at least as large as the thickness d of the measured object, taking into consideration the indexes of refraction $n_g$ or $n_e$ for the object 1 and for the element 15.

FIGS. 5 and 6 show the path differences as obtained by means of the above example, as well as the illustration located below, which indicate the path length modification per second (time unit) ▲s/t at 2.5 Hz rotation frequency of the element 15 around the rotation angle α. Depending upon the width a of the coatings 40a to 40d, the actual values for the path difference ▲s, as well as the path length modification per second ▲s/t, start at higher angular values (for example, in the case of FIG. 3, only at approximately 20°) and end already below 90° (for example, approximately 50° in the example). Larger angular areas can be obtained if the coatings 40a to 40d are omitted.

An index of refraction of $n_e$=1.5 or 2.5 for the medium of the element 15 is the parameter in FIG. 5 or 6. As can be seen in FIGS. 5 and 6, a good linearity of the path length modification per second with a deviation of merely approximately 3 % can be obtained for the above example with a refraction index $n_e$ of the medium of $n_e$=2.5.

An object at almost any desired distance from the coupling 17 and the evaluation unit 10 corresponding thereto can be measured by using both radiation guides 20a and 20b. If, for example, the thickness of the human cornea is being determined, then the coupling 17, both polarization control units 19a and 19b, the radiation source 3, the radiation detector 7, the reflector 30, the lens 31, the element 15, and the evaluation unit 10 are preferably installed in the device, and a preset radiation guide 20b can be coupled for path adaptation. The measuring unit 23 is placed then immediately in front of the human eye and connected to the device by means of a suitable length of the radiation guide 20a. Other transparent objects, such as films, coatings, plates, layers of plates, etc. can also be measured instead of the human cornea.

Not only can the thickness d, that is, not only the distance of reflections on two surfaces, of a "plate" be determined with the apparatus of the invention, but also the distances of several superposed surfaces. Distances to delimiting surfaces in a diffused medium or expansions of diffused zones can also be determined by means of the apparatus.

Other cylinders with multiple edges, or cross-sectional surfaces building a regular polygon, wherein a reference beam comes to rest, can be utilized instead of the above-described four-corner cube. An octagon, for example, is represented in FIG. 7. However, a reflector 44 similar to the reflector 30 is not longer arranged on the side of the element where the beam 41a enters, but is displaced by 90 . FIG. 8 shows a diagram for the octagon 43 of FIG. 7 similar to the one shown in FIG. 6. The radiation frequency amounts here to 4 Hz, the index of refraction $n_e$=2.5 (ZnSe), and the distance e from the entering beam 41a to the surface width $1_0$=30 mm. The cylinder jacket surfaces 46 are preferably provided with a coating that depends heavily on the entering angle of the beam.

What is claimed is:

1. An apparatus configured as a Michelson interferometer for measuring thickness of a transparent object, comprising:
    a radiation source for generating radiation having short coherence length;
    a measuring arm having the object arranged at a first end thereof;
    a reference arm having a reflector arranged at a first end thereof;
    an observation arm having a radiation detector arranged at a first end thereof;
    a coupling unit, coupling said radiation source and second ends of said measuring, reference, and observation arms, for dividing the radiation from said source into said measuring arm and said reference arm and for combining radiation reflected by the object and the reflector, by interference and coupling, into said observation arm; and
    a path length variation element arranged between the reflector and said coupling unit along said reference arm, said path length variation element being optically transparent for the radiation, being rotatable about a rotational axis thereof, having at least four side walls and having an axis of symmetry identical with the rotational axis,
    the rotational axis of said path length variation element being arranged perpendicular to a propagation direction of the radiation incident on said path length variation element from said coupling unit, the incident radiation being reflected at least twice at inner side walls of said path length variation element.

2. The apparatus of claim 1, wherein the radiation incident from said coupling unit propagates on a cross-sectional plane area inside said path length variation element,
    the cross-sectional plane area being bordered by the at least four side walls and having a contour of a regular polygon.

3. The apparatus of claim 2, wherein the cross-sectional plane area is perpendicular to the rotational axis, the radiation incident from said coupling unit having a variable entrance location on the at least four side walls that is displaced a preset distance sideways from the rotational axis.

4. An apparatus configured as a Michelson interferometer for measuring thickness of a transparent object, comprising:
    a radiation source for generating radiation having short coherence length;
    a measuring arm having the object arranged at a first end thereof;

a reference arm having a reflector arranged at a first end thereof;

an observation arm having a radiation detector arranged at a first end thereof;

a coupling unit, coupling said radiation source and second ends of said measuring, reference, and observation arms, for dividing the radiation from said source into said measuring arm and said reference arm and for combining radiation reflected by the object and the reflector, by interference and coupling, into said observation arm; and a path length variation element arranged between the object and said coupling unit along said measuring arm, said path length variation element being optically transparent for the radiation, being rotatable about a rotational axis thereof, having at least four side walls and having an axis of symmetry identical with the rotational axis, the rotational axis of said path length variation element being arranged perpendicular to a propagation direction of the radiation incident on said path length variation element from said coupling unit, the incident radiation being reflected at least twice at inner side walls of said path length variation element.

5. The apparatus of claim 4, wherein the radiation incident from said coupling unit propagates on a cross-sectional plane area inside said path length variation element, the cross-sectional plane area being bordered by the at least four side walls and having a contour of a regular polygon.

6. The apparatus of claim 5, wherein the cross-sectional plane area is perpendicular to the rotational axis, the radiation incident from said coupling unit having a variable entrance location on the at least four side walls that is displaced a preset distance sideways from the rotational axis.

7. An apparatus configured as a Michelson interferometer for measuring thickness of a transparent object, comprising:

a radiation source for generating radiation having short coherence length;

a measuring arm having the object arranged at a first end thereof;

a reference arm having a reflector arranged at a first end thereof;

an observation arm having a radiation detector arranged at a first end thereof;

a coupling unit, coupling said radiation source and second ends of said measuring, reference, and observation arms, for dividing the radiation from said source into said measuring arm and said reference arm and for combining radiation reflected by the object and the reflector, by interference and coupling, into said observation arm; and first and second path length variation elements optically transparent for the radiation, being rotatable about respective rotational axes thereof, each having at least four side walls and each having an axis of symmetry identical with the respective rotational axis, said first path length variation element being arranged between the reflector and said coupling unit along said reference arm and said second path length variation element being arranged between said object and said coupling unit along said measuring arm, the rotational axes of said path length variation elements being arranged perpendicular to a propagation direction of the radiation incident on said path length variation elements from said coupling unit, the incident radiation being reflected at least twice at inner side walls of said path length variation elements, the rotational axes of said path length variation elements being contrary.

8. The apparatus of claim 7, wherein the radiation incident from said coupling unit propagates on cross-sectional plane areas inside said path length variation elements, the cross-sectional plane areas being bordered by the respective at least four side walls and having a contour of a regular polygon.

9. The apparatus of claim 8, wherein the cross-sectional plane areas are perpendicular to the respective rotational axes, the radiation incident from said coupling unit having variable entrance locations on the respective at least four side walls that are displaced a preset distance sideways from the respective rotational axes.

* * * * *